United States Patent [19]
Inaba

[11] 4,182,343
[45] Jan. 8, 1980

[54] DOUBLE COELIAC DRAINAGE TUBE MADE OF SILICONE

[75] Inventor: Yutaka Inaba, Tokyo, Japan

[73] Assignee: President of Tokyo Medical and Dental University, Tokyo, Japan

[21] Appl. No.: 836,907

[22] Filed: Sep. 26, 1977

[30] Foreign Application Priority Data

Oct. 5, 1976 [JP] Japan .................................. 51-118947

[51] Int. Cl.² .......................................... A61M 27/00
[52] U.S. Cl. ............................................. 128/350 R
[58] Field of Search ............................ 128/348–351, 128/276–278, 252

[56] References Cited

U.S. PATENT DOCUMENTS

| | | | |
|---|---|---|---|
| 1,656,157 | 1/1928 | Correnti | 128/252 |
| 2,614,563 | 10/1952 | Devine | 128/276 |
| 3,020,913 | 2/1962 | Heyer | 128/350 V |
| 3,314,430 | 4/1967 | Alley et al. | 128/350 R |
| 3,528,427 | 9/1970 | Sheridan et al. | 128/350 R |
| 3,626,950 | 12/1971 | Schulte | 128/350 R |
| 3,771,527 | 11/1973 | Ruisi | 128/350 R |

Primary Examiner—Dalton L. Truluck
Attorney, Agent, or Firm—Wenderoth, Lind & Ponack

[57] ABSTRACT

A silicon double body cavity drain tube having a double tubular structure at one end. A silicon rubber outer tube having one end sealed and the other end open is provided around a silicon rubber inner tube that is shorter than the outer tube. One end of the inner tube is fixed to the inner wall of the sealed end of the outer tube and the other end of the inner tube is open and may or may not be fixed to the inner wall of the outer tube. Also, the outer tube and the inner tube, respectively, have a plurality of holes passing through their respective sidewalls, the holes through the outer tube sidewall being positioned in such a manner so that they do not align with the holes in the sidewall of the inner tube.

2 Claims, 9 Drawing Figures

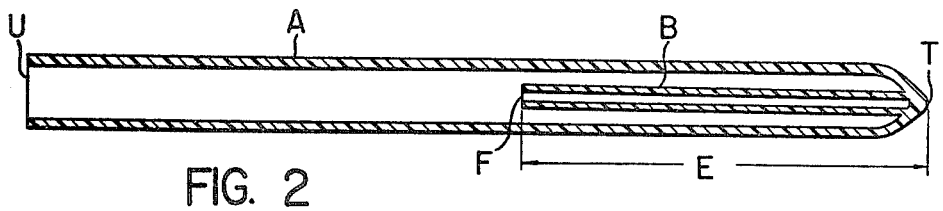
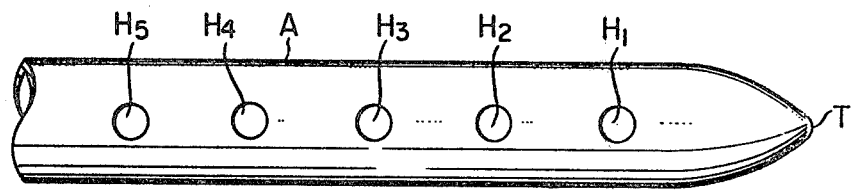
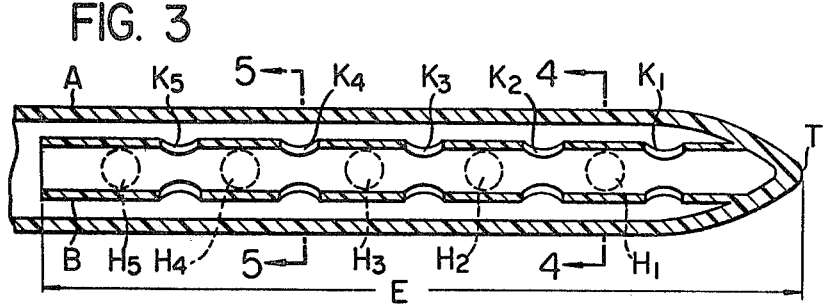
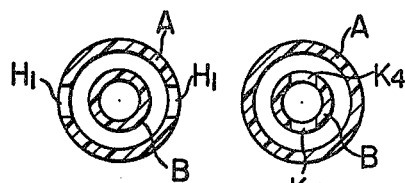
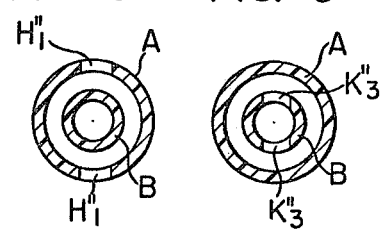
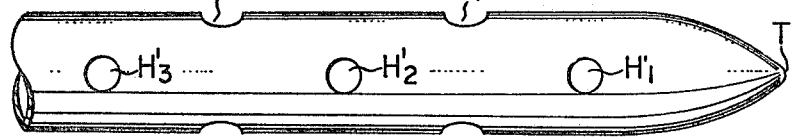
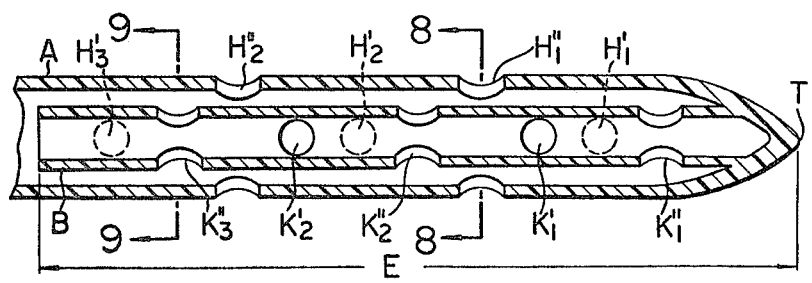

DOUBLE COELIAC DRAINAGE TUBE MADE OF SILICONE

BACKGROUND OF THE INVENTION

This invention relates to a body cavity drain tube used for drainage purposes. In particular, a ventricular tube is discussed, but it should be noted that this invention is not limited thereto. The drain tube of this invention is used as a head for a ventricular tube, and is particularly suitable for removing cerebrospinal fluid from a ventricle.

A ventricular tube, a catheter, having many sidewall holes in its head part and used for the above-mentioned purpose is well known, but these sidewall holes are often blocked by choroid plexus which penetrate into the ventricular tube through the holes. In order to prevent this blockage, various devices have been proposed. For example, a catheter having a curved head part (Japanese Patent Publication No. 44-18711) and a catheter having a head part with many fins protruding vertically with respect to the tube axis (Japanese Laid Open Application No. 48-18711) have been devised.

However, the effect of preventing the blockage of a ventricular tube is still small even with these devices. That is, even with the above-mentioned modified catheters, it is impossible to completely prevent choroid plexus from penetrating into the inside of the catheter through its sidewall holes. Once the choroid plexus penetrates into the inside of the catheter through the sidewall holes in the lowest part of the catheter, the catheter is rapidly blocked and the draining function is completely inhibited, even if the other holes remain open. Thus, the development of a ventricular tube capable of providing a stable and constant drain function has been required.

SUMMARY OF THE INVENTION

This invention solves the above-mentioned problems with regard to the conventional ventricular tubes.

This invention relates to a silicon, double-body cavity drain tube having a double pipe structure end which comprises a silicon rubber outer tube having one end sealed and the other end open, and a silicon rubber inner tube shorter than the outer tube, one end of which is fixed to the inner wall of the sealed end of the outer tube and the other end of which is open and either fixed or not fixed to the inner wall of the outer tube. The outer tube and the inner tube, respectively, have a plurality of holes passing through their respective tube walls, the holes of the outer tube wall being positioned in such a manner so as not to correspond to those of the inner tube wall.

The double ventricular tube of the present invention is different from the above-mentioned conventional catheters, and the inside space of the inner tube and a gap between the outer tube and the inner tube are not blocked. Therefore, provided that at least one of the sidewall holes of the outer tube is open, the drainage function of removing cerebrospinal fluid is sufficiently maintained even if all the other sidewall holes are blocked. Thus, the double ventricular drain tube of this invention is much more effective than the conventional catheters.

In the ventriculoatrial shunt or ventriculoperitoneal shunt ordinarily used to treat hydrocephalus, if a ventricular tube or catheter is inserted to a great depth, choroid plexus tends to more frequently penetrate into the tube. On the other hand, if the ventricular tube is inserted only a short distance (to an anterior horn of the ventricle) brain substance tends to penetrate into the tube, thereby blocking the tube since the brain mantle (the brain substance layer) becomes thick due to the shrinkage of the ventricle caused by drainage. Accordingly the sidewall holes of the ventricular tube are faced with the brain substance layer.

The double ventricular drain tube of this invention solves the above-mentioned dilemma and provides an excellent structure which does not cause the above-mentioned two kinds of blockage problems even if the tube is inserted to a great depth.

BRIEF DESCRIPTION OF THE DRAWINGS

The double ventricular drain tube is more fully illustrated by referring to the accompanying drawings wherein:

FIG. 1 shows a sectional view of a double ventricular tube of this invention;

FIG. 2 shows a partial view of the head part of the outer tube of the ventricular tube of this invention;

FIG. 3 is a partial sectional view of the head part of the ventricular tube of this invention, which corresponds to FIG. 2;

FIGS. 4 and 5 show cross-sectional views of the ventricular tube of this invention cut along the lines 4—4 and 5—5 in FIG. 3;

FIG. 6 is a view similar to FIG. 2, which shows another embodiment of the ventricular tube of this invention;

FIG. 7 is a view similar to FIG. 3, which corresponds to FIG. 6;

FIGS. 8 and 9 show cross-sectional views of the ventricular tube cut along the lines 8—8 and 9—9 in FIG. 7.

DETAILED DESCRIPTION OF THE INVENTION

FIG. 1 shows a sectional view of a double-body cavity drain tube, for example the double ventricular drain tube of this invention. A head part E of the ventricular drain tube of this invention has a double tube structure comprising an outer tube A and an inner tube B, the end opposite an open end F of the inner tube B being fixed to the inner wall of a sealed end T of the outer tube A. The open end F of the inner tube B may or may not be fixed to the inside wall of the outer tube by a bonding agent or other appropriate means. As shown in the drawing, the sealed end T of the outer tube A preferably has a spherical or conical shape. The head part of the ventricular drain tube must be inserted through brain substance in such a manner as to reach the ventricle. The reasons why the end T is sealed are: (1) to prevent small pieces of soft brain stubatance from entering into the tube and (2) to allow insertion to proceed smoothly. It should be noted that the sealed end may have various other shapes depending on the specific requirements. The ventricular tube of this invention is characterized in that it has a head part E with a double tube structure comprising an outer tube and an inner tube and in that the outer and inner tubes of the head part E have many sidewall holes. The sidewall holes of the outer tube are out of alignment with the sidewall holes of the inner tube. The positions of the sidewall holes of the outer tube A and the inner tube B of the head part E are not specifically limited, but they must not overlap each other. FIG. 2 and the other figures show various embodiments of the positions of the sidewall holes, but this invention is not limited thereto. FIG. 2 is a partial view of the head part of a body cavity drain tube, for example the double ventricular drain tube of this invention, wherein the sidewall holes H of the outer tube A are represented by a series of holes $H_1$, $H_2$, $H_3$, $H_4$ and $H_5$ which penetrate through in a direction of 90° with respect to the plane of the paper. FIG. 3 is a parial sectional view of the head part of the ventricular tube of this invention, which corresponds to FIG. 2. In FIG. 3, the sidewall holes K of the inner tube B are represented by a series of holes $K_1$, $K_2$, $K_3$, $K_4$ and $K_5$ which are open in a direction parallel to the plane of the paper. FIGS. 4 and 5 respectively show cross-sectional view of the ventricular tube cut along the lines 4—4 and 5—5 in FIG. 3. As can be seen from FIGS. 2, 3, 4 and 5, the sidewall holes H of the outer tube A and the sidewall holes K of the inner tube B do not overlap each other and practically cross each other at 90° angles. FIG. 6 is a partial view showing another embodiment of the head part E of the outer tube of the ventricular tube of this invention. Sidewall holes H' and H" in the outer tube are positioned in such a manner as to make the opening directions of the two sets of holes cross each other at 90°. FIG. 7 is a partial sectional view of the head part of the ventricular tube of this invention and corresponds to FIG. 6. Sidewall holes K' and K" of the inner tube B are also positioned at 90° to each other and in such a manner as not to overlap the sidewall holes H' and H" of the outer tube A; that is, they are positioned between the holes H' and H". The opening direction of the holes K' is at 90° with respect to the plane of the paper, and their positions do not overlap with the positions of any of the holes H' and H". FIGS. 8 and 9 show cross-sectional views of the tube cut along the lines 8—8 and 9—9 in FIG. 7. As can be seen from FIGS. 8 and 9, the opening directions of the sidewall holes of both of the inner and outer tubes are at 90° to each other and their positions do not overlap.

It is not necessary to limit the length of the head part E of the ventricular tube having the double tube structure of this invention, but the length of the head part E is preferably about 2–3 cm, e.g., about 2.5 cm. The diameter of the outer tube of the ventricular tube of this invention may be the same as that of the conventional ventricular tube, but preferably it should have an outside diameter of 2–3 mm and an inside diameter of 1.5–2 mm, and the inner tube should have an outside diameter of 1.19–1.30 mm and an inside diameter of 0.64–0.90 mm.

The ventricular tube of the present invention is produced from elastic material for medical use, for example silicon rubber and other synthetic resin elastic materials can also be used.

In clinical use, the head part E is inserted into a ventricle, and the end U as shown in FIG. 1 is connected to other tubes, an embedded tank mechanism or the like (see Japanese Patent Publication No. 44-18712).

As mentioned above, the advantage of the ventricular tube of this invention is that the desired function of the ventricular tube of this invention is not lost since choroid plexus of the ventricle does not penetrate into the inner space of the inner tube through its sidewall holes even if choroid plexus enters into the ventricular tube through the sidewall holes of the outer tube. As compared with the simplest conventional ventricular tube, the degree of penetration of the tube of this invention into brain tissue is almost the same and its manipulation is also easy. Besides, the tube of this invention is made of an elastic material, and accordingly its manipulation is even easier.

This invention is further illustrated by the following example.

Ventricular tubes having a 25 mm long head part and of the various sizes as mentioned in the following Table 1 were tested. The heads of the respective ventricular tubes were placed in a water tank with their ends U protruding out of the tank. The fall "h" was adjusted at 50 mm and 75 mm respectively and the other tubes were arranged in the following manners: all the sidewall holes were open; half the sidewall holes were open; only two of the sidewall holes were open; and only one of the sidewall holes was open. Under these conditions, the amounts of water flowing out of the respective ends U per minute were measured. The results are shown in the following Table 2. As can be seen from Table 2, the drainage amount in the case of only one of the holes being open was at least 35% of that in the case of all the holes being open. The drainage amount of the drain tube having the same size as the conventional drain tube was 4.5 ml in the case of only one of the holes being open, and this value was proved to be fully useful for practical use. Thus, the amount of cerebrospinal fluid drained from a ventricle by means of the ventricular tube of this invention even under the worst conditions is fully satisfactory in view of clinical requirements.

Table 1

|  |  | Tube Size | | |
|---|---|---|---|---|
|  |  | A | B | C |
| Inner tube | Inside diameter (mm) | 0.64 | 0.64 | 0.64 |
|  | Outside diameter (mm) | 1.19 | 1.19 | 1.19 |
|  | The diameter of the side wall hole (mm) | 0.4–0.7 | 0.4–0.7 | 0.4–0.7 |
|  | The number of side wall holes | 10 | 10 | 10 |
| Outer tube | Inside diameter (mm) | 2.00 | 2.00 | 1.57 |
|  | Outside diameter (mm) | 3.00 | 3.00 | 2.41 |
|  | The diameter of the side wall hole | 0.5–1.0 | 0.5–1.0 | 0.5–1.0 |
|  | The number of side wall holes | 10 | 20 | 10 |

Table 2

Remarks : Flow amount (ml/min.)

| Type | h | The number of side wall holes of the outer tube | All the holes open | Half the holes open | Two of the holes open | One of the holes open |
|---|---|---|---|---|---|---|
| A | 175 mm |  | 56.0 (100%) | 52.0 (93%) | 47 | 46.0 (82%) |
|  | 50 mm |  | 27.0 | 25.0 (93%) | 24.0 | 22.5 (83%) |
| B | 175 mm |  | 46.0 (100%) | 46.0 (100%) | 40 | 39.0 (85%) |
|  | 50 mm |  | 24.0 | 22.5 (94%) | 16.5 | 16.0 (67%) |
|  | 175 mm |  | 28.0 | 25.0 | 20.0 | 19.0 |

Table 2-continued

| Type | h | The number of side wall holes of the outer tube | All the holes open | Half the holes open | Two of the holes open | One of the holes open |
|---|---|---|---|---|---|---|
| C | | | (100%) | (89%) | | (68%) |
| | 50 mm | | 13.0 (100%) | 9.0 (69%) | 7.0 | 4.5 (35%) |

Choroid plexus taken from a human body at the time of autopsy soon after death was suspended in a physiological saline solution, and was adsorbed into the ventricular tube of this invention under vacuum. According to this experiment, it was found that a part of the choroid plexus penetrated into the ventricular tube through the sidewall holes of the outer tube, but did not block the sidewall holes of the inner tube. It can be expected from this experiment that the drainage function of the ventricular tube of this invention is quite satisfactory in view of clinical requirements, unless all of the holes of the outer tube of the ventricular tube of this invention are blocked.

Ventriculoatrial shunts and ventriculoperitoneal shunts were applied to eight adults and children suffering from hydrocephalus using the ventricular tube of this invention, and none of the tubes became blocked during the first nine months after the operation. Thus, the rate of blockage of the ventricular tube of this invention is notably low as compared with the conventional ventricular tube.

What is claimed is:

1. A double body cavity drain tube comprising:
   an outer tube having one end closed and one end open, said outer tube having a plurality of openings therethrough; and
   an inner tube shorter than said outer tube positioned within said outer tube and one end of said inner tube being connected to the inner wall of said outer tube at said closed end thereof, said inner tube further having a plurality of openings therethrough along a substantial portion of the length thereof, all of said openings in said inner tube being out of alignment with said openings in said outer tube.

2. A double body cavity drain tube as claimed in claim 1, wherein said inner and outer tubes are comprised of silicon.

* * * * *